US012749191B2

(12) United States Patent
Novosel

(10) Patent No.: US 12,749,191 B2
(45) Date of Patent: Sep. 29, 2026

(54) MULTIMODAL PREDICTION OF VISUAL ACUITY RESPONSE

(71) Applicant: HOFFMANN-LA ROCHE INC., Little Falls, NJ (US)

(72) Inventor: Jelena Novosel, Brugg (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 478 days.

(21) Appl. No.: 18/328,296

(22) Filed: Jun. 2, 2023

(65) Prior Publication Data

US 2023/0394667 A1 Dec. 7, 2023

Related U.S. Application Data

(63) Continuation of application No. PCT/US2021/061595, filed on Dec. 2, 2021.
(Continued)

(51) Int. Cl.

| | |
|---|---|
| ***A61B 5/00*** | (2006.01) |
| ***A61B 3/10*** | (2006.01) |
| ***G06T 7/00*** | (2017.01) |
| ***G06V 10/82*** | (2022.01) |
| ***G16H 30/20*** | (2018.01) |

(52) U.S. Cl.
CPC .......... *G06T 7/0014* (2013.01); *A61B 5/4848* (2013.01); *G16H 30/20* (2018.01); *G06T 2200/04* (2013.01); *G06T 2207/10024* (2013.01); *G06T 2207/10101* (2013.01);
(Continued)

(58) Field of Classification Search
CPC ............... G06T 7/0014; G06T 2200/04; G06T 2207/10024; G06T 2207/10101; G06T 2207/20084; G06T 2207/20221; G06T 2207/30041; A61B 5/4848; A61B 3/0025; A61B 3/102; A61B 3/12; G16H 30/20;
(Continued)

(56) References Cited

U.S. PATENT DOCUMENTS

| | | | | |
|---|---|---|---|---|
| 11,195,271 | B2 * | 12/2021 | Chauhan | G06T 7/0012 |
| 12,112,480 | B2 * | 10/2024 | Boyd | A61B 3/12 |

(Continued)

FOREIGN PATENT DOCUMENTS

| | | | |
|---|---|---|---|
| JP | 2013-027439 | A | 2/2013 |
| JP | 2019528826 | A | 10/2019 |

(Continued)

OTHER PUBLICATIONS

McIntosh, Lane, et al. "Deep learning models of the retinal response to natural scenes." Advances in neural information processing systems 29 (2016).*

(Continued)

*Primary Examiner* — Shefali D Goradia
(74) *Attorney, Agent, or Firm* — Haynes and Boone, LLP

(57) ABSTRACT

Methods and systems for predicting visual acuity response are provided. The methods and systems utilize one or more of a first input that includes two-dimensional imaging data and a second input that includes three-dimensional imaging data. A visual acuity response (VAR) output is predicted, via a neural network system, using the first input and/or the second input. The VAR output comprises a predicted change in visual acuity of a subject undergoing a treatment.

21 Claims, 8 Drawing Sheets

Related U.S. Application Data

(60) Provisional application No. 63/175,544, filed on Apr. 15, 2021, provisional application No. 63/121,213, filed on Dec. 3, 2020.

(52) U.S. Cl.
CPC ............... *G06T 2207/20084* (2013.01); *G06T 2207/20221* (2013.01); *G06T 2207/30041* (2013.01)

(58) Field of Classification Search
CPC ... G06V 10/82; G06V 2201/03; G06V 10/811
See application file for complete search history.

(56) References Cited

U.S. PATENT DOCUMENTS

| | | | | |
|---|---|---|---|---|
| 2018/0084988 | A1 | 3/2018 | Chakravorty et al. | |
| 2019/0150727 | A1* | 5/2019 | Blaha | A61B 3/024 |
| 2020/0085882 | A1 | 3/2020 | Cuzzani et al. | |
| 2022/0230300 | A1* | 7/2022 | Kawczynski | G06T 7/0004 |
| 2023/0025980 | A1* | 1/2023 | Kawczynski | G06T 7/187 |
| 2024/0339191 | A1* | 10/2024 | Kikuchi | A61B 3/0025 |

FOREIGN PATENT DOCUMENTS

| | | | | |
|---|---|---|---|---|
| JP | 2020-039851 | A1 | 3/2020 | |
| JP | 20200511539 | A | 4/2020 | |
| WO | 2020210891 | A1 | 10/2020 | |
| WO | WO-2021026039 | A1 * | 2/2021 | G06N 3/045 |

OTHER PUBLICATIONS

Kawczynski, Michael G., et al. "Development of deep learning models to predict best-corrected visual acuity from optical coherence tomography." Translational vision science & technology 9.2 (2020): 51-51.*

Rasti, Reza, et al. "Deep learning-based single-shot prediction of differential effects of anti-VEGF treatment in patients with diabetic macular edema." Biomedical optics express 11.2 (2020): 1139-1152.*

International Search Report and Written Opinion mailed Mar. 23, 2022 in International Application No. PCT/US2021/061595, 10 pages.

International Preliminary Report on Patentability issued May 30, 2023 in International Application No. PCT/US2021/061595, 7 pages.

Reza et al., "Deep Learning-Based Single-Shot Prediction of Differential Effects of Anti-VEGF Treatment in Patients with Diabetic Macular Edema", Biomedical Optics Express, Jan. 28, 2020, pp. 1139-1152, vol. 11, No. 2.

Yoo et al., "The Possibility of the Combination of OCT and Fundus Images for Improving the Diagnostic Accuracy of Deep Learning for Age-Related Macular Degeneration: A Preliminary Experiment", Medical & Biological Engineering & Computing, Oct. 22, 2018, pp. 677-687, vol. 57.

Abramoff et al., "Retinal Imaging and Image Analysis", IEEE Reviews in Biomedical Engineering, Jan. 1, 2010, pp. 169-208, vol. 3.

Kaiser, "Ranibizumab for the Treatment of Neovascular AMD," International Journal of Clinical Practice, Mar. 2007, pp. 501-509, vol. 61, No. 3.

Shao et al., "Neovascular Age-Related Macular Degeneration," Developments in Ophthalmology, Oct. 2016, pp. 125-136, vol. 55.

Parfitt et al., "Patient-Reported Reasons for Delay in Diagnosis of Age-Related Macular Degeneration: A National Survey," BMJ Open Ophthalmology, 2019, e000276, vol. 4, Issue 1.

Martin et al., "CATT Research Group," The New England Journal of Medicine, May 19, 2011, pp. 1897-1908, vol. 364, No. 20.

Lin et al., Focal Loss for Dense Object Detection, Feb. 7, 2018, arXiv:1708.020022.

Schlemper et al., "Attention Gated Networks: Learning to Leverage Salient Regions in Medical Images," Medical Image Analysis, Apr. 2019, pp. 197-207, vol. 53.

Office Action mailed Aug. 19, 2025 in related Japanese Application 2023-533641, 6 pages.

Decision to Grant and English Translation for related Japanese Patent Application No. 2023-533641, dated Mar. 17, 2026, 6 pages.

* cited by examiner

MULTIMODAL PREDICTION OF VISUAL ACUITY RESPONSE

CROSS-REFERENCE TO RELATED APPLICATIONS

The present application is a continuation of International Application No. PCT/US2021/061595, filed Dec. 2, 2021, which claims priority to U.S. Provisional Patent Application No. 63/121,213, filed on Dec. 3, 2020, entitled "MULTI-MODAL PREDICTION OF VISUAL ACUITY RESPONSE" and to U.S. Provisional Patent Application No. 63/175,544, filed on Apr. 15, 2021, entitled "MULTI-MODAL PREDICTION OF VISUAL ACUITY RESPONSE," which applications are incorporated herein by reference in their entireties for all purposes.

FIELD

This description is generally directed towards predicting visual acuity response in subjects diagnosed with age-related macular degeneration (AMD). More specifically, this description provides methods and systems for predicting visual acuity response in subjects diagnosed with AMD using information obtained from one or more imaging modalities.

INTRODUCTION

Age-related macular degeneration (AMD) is a disease that impacts the central area of the retina in the eye, which is referred to as the macula. AMD is a leading cause of vision loss in subjects 50 years or older. Neovascular AMD (nAMD) is one of the two advanced stages of AMD. With nAMD, new and abnormal blood vessels grow uncontrollably under the macula. This type of growth may cause swelling, bleeding, fibrosis, other issues, or a combination thereof. The treatment of nAMD typically involves an anti-vascular endothelial growth factor (anti-VEGF) therapy (e.g., an anti-VEGF drug such as ranibizumab). The retina's response to such treatment is at least partially subject specific, such that different subjects may respond differently to the same type of anti-VEGF drug. Further, anti-VEGF therapies are typically administered via intravitreal injections, which can be expensive and themselves cause complications (e.g., blindness). Thus, there is a need for systems and methods that can predict how well a subject having nAMD is likely to respond to treatment with an anti-VEGF drug.

SUMMARY

The present disclosure provides systems and methods for predicting visual acuity response (VAR). The systems and methods generally utilize neural networks. In some embodiments, the systems and methods utilize neural networks configured to receive an input comprising two-dimensional (2D) imaging data, such as color fundus imaging (CFI) data, and to apply a trained model to the input to predict a VAR response (such as a predicted change in visual acuity of the subject in response to undergoing a treatment, such as treatment with an anti-VEGF drug). In some embodiments, the systems and methods utilize neural networks configured to receive an input comprising three-dimensional (3D) imaging data, such as optical coherence tomography (OCT) data and to apply a trained model to the input to predict a VAR response. In some embodiments, the methods and systems are configured to receive a first input that includes 2D imaging data and a second input that includes 3D imaging data and to apply a trained model to the first and second inputs to predict a VAR response.

BRIEF DESCRIPTION OF THE DRAWINGS

For a more complete understanding of the principles disclosed herein, and the advantages thereof, reference is now made to the following descriptions taken in conjunction with the accompanying drawings, in which.

Figure 1:
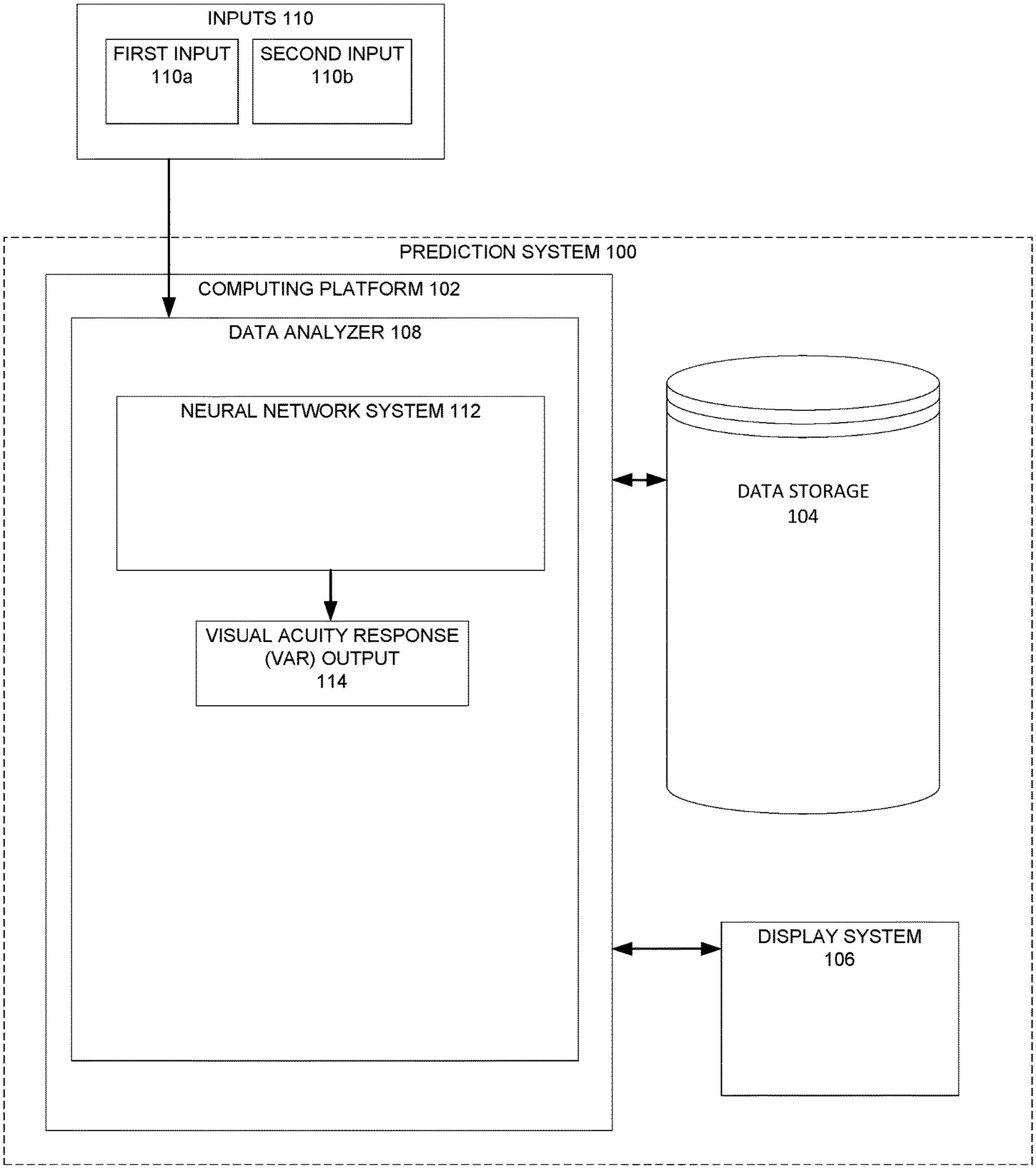
FIG. 1 is a block diagram of a prediction system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Overview

Determining a subject's response to an age-related macular degeneration (AMD) treatment may include determining that subject's visual acuity response (VAR). A subject's visual acuity is the sharpness of his or her vision, which may be measured by the subject's ability to discern letters or numbers at a given distance. Visual acuity is oftentimes ascertained via an eye exam and measured according to the standard Snellen eye chart. However, other measures of visual acuity may be utilized in place of the Snellen eye chart. Retinal images may provide information that can be used to estimate a subject's visual acuity. For example, color fundus (CF) images may be used to estimate a subject's visual acuity at the time the color fundus images were captured.

But in certain cases, such as, for example, in clinical trials, being able to predict a subject's future visual acuity in response to an AMD treatment may be desirable. For example, it may be desirable to predict whether a subject's visual acuity will have improved at a selected period of time after treatment (e.g., at 3, 6, 9, or 12 months after treatment, etc.). Further, it may be desirable to classify any such predicted improvement in visual acuity. Such predictions and classification may enable treatment regimens to be personalized for a given subject. For example, predictions about a subject's visual acuity response to a particular AMD treatment may be used to customize the treatment dosage (such as the injection dosage), the intervals at which treatments (such as injections) are given, or both. Further, such predictions may improve clinical trial screening, prescreening, or both by enabling the exclusion of those subjects predicted to not respond well to treatment.

Thus, the various embodiments described herein provide methods and systems for predicting visual acuity response to an AMD treatment. In particular, imaging data from one or more imaging modalities is received and processed by a neural network system to predict a visual acuity response (VAR) output. The VAR output may comprise a predicted change in the visual acuity of a subject undergoing treatment. In some cases, the VAR output corresponds to the predicted change in visual acuity in that the VAR output may be further processed to determine this predicted change. Thus, the VAR output may be an indicator of the predicted change in visual acuity. In one or more embodiments, these different imaging modalities include color fundus imaging and/or optical coherence tomography (OCT).

Color fundus imaging is a two-dimensional imaging modality. Color fundus imaging captures about a 30-degree to about a 50-degree view of the retina and optic nerve. In addition to being widely available and easy to use, color fundus imaging may be better at capturing the appearance of the optic nerve and the existence of blood buildup in the eye as compared to other imaging modalities. However, color fundus imaging may be unable to capture thickness or volumetric data about the retina.

OCT may be considered a three-dimensional imaging modality. In particular, OCT may be used to capture images with micrometer (e.g., at most about 10 μm, 9 μm, 8 μm, 7 μm, 6 μm, 5 μm, 4 μm, 3 μm, 2 μm, 1 μm, or higher resolution, at least about 1 μm, 2 μm, 3 μm, 4 μm, 5 μm, 6 μm, 7 μm, 8 μm, 9 μm, 10 μm, or lower resolution, or resolution within a range defined by any two of the preceding values) resolution that provide depth information. OCT images may provide thickness and/or volumetric information about the retina that cannot be ascertained or that cannot be easily or accurately ascertained using color fundus imaging. For example, OCT images may be used to measure the thickness of the retina. Further, OCT images may be used to reveal and distinguish between fluid in the retina and fluid underneath the retina (e.g., subretinal fluid). Still further, OCT images may be used to identify the locations of abnormal new vessels in the eye. But OCT images may be less accurate in identifying blood buildup as compared to color fundus imaging.

Various embodiments provided herein recognize that neural networks trained using color fundus images alone or OCT images alone may achieve sufficient accuracy, precision, and/or recall metrics to provide reliable VAR predictions of a response to an AMD treatment. Such neural networks may be especially valuable when only one of the color fundus images and the OCT images is available for a particular subject.

Various embodiments provided herein recognize that each of color fundus imaging and OCT may provide more accurate information about at least one retinal feature as compared to the other of these two imaging modalities. Accordingly, various embodiments described herein recognize that using the information provided by both of these different imaging modalities may enable improved VAR predictions of a response to an AMD treatment as compared to using each imaging modality independently. Such a multimodal approach, may generally enable faster, more efficient, and more accurate predictions of visual acuity response as compared to at least some of the currently available methodologies for predicting AMD treatment outcomes.

Recognizing and taking into account the importance and utility of a methodology and system that can provide the improvements described above, the specification describes various embodiments for predicting VAR to an AMD treatment. More particularly, the specification describes various embodiments of methods and systems for processing imaging data, obtained via one or two different imaging modalities, using a neural network system (e.g., a convolutional neural network system) to generate a VAR output that enables predicting a future visual acuity of a subject at a selected period of time after treatment.

Moreover, the present embodiments facilitate the creation of personalized treatment regimens for individual subjects to ensure the proper dosage and/or intervals between injections. In particular, the single mode and multi-modal approaches to predicting VAR presented herein may help generate accurate, efficient, and/or expedient personalized treatment and/or dosing schedules and enhance clinical cohort selection and/or clinical trial design.

Definitions

The disclosure is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

In addition, as the terms "on," "attached to," "connected to," "coupled to," or similar words are used herein, one element (e.g., a component, a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

The term "subject" may refer to a subject of a clinical trial, a person undergoing treatment, a person undergoing anti-cancer therapies, a person being monitored for remission or recovery, a person undergoing a preventative health analysis (e.g., due to their medical history), or any other person or patient of interest. In various cases, "subject" and "patient" may be used interchangeably herein.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology and toxicology are described herein are those well-known and commonly used in the art.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

As used herein, the term "or" may include both disjunctive and conjunctive meanings. That is, the phrase "A or B" may refer to A only, B only, or both A and B.

In the Figures, like numbers refer to like elements.

As used herein, a "model" may include one or more algorithms, one or more mathematical techniques, one or more machine learning algorithms, or a combination thereof.

As used herein, "machine learning" includes the practice of using algorithms to parse data, learn from it, and then make a determination or prediction about something in the world. Machine learning uses algorithms that can learn from data without relying on rules-based programming.

As used herein, an "artificial neural network" or "neural network" (NN) may refer to mathematical algorithms or computational models that mimic an interconnected group of artificial neurons that processes information based on a connectionistic approach to computation. Neural networks, which may also be referred to as neural nets, can employ one or more layers of linear units, nonlinear units, or both to predict an output for a received input according to mathematical operations defined by parameters or weight factors determined in a training mode described herein. Some neural networks include one or more inner or hidden layers in addition to an output layer. The output of each inner or hidden layer may be used as input to the next layer in the network, i.e., the next inner or hidden layer or the output layer. Each layer of the network generates an output from a received input in accordance with current values of a respective set of parameters. In the various embodiments, a reference to a "neural network" may be a reference to one or more neural networks.

A neural network may process information in two ways; when it is being trained it is in training mode and when it puts what it has learned into practice it is in inference (or prediction) mode. Neural networks may learn through a feedback process (e.g., backpropagation) which allows the network to adjust the weight factors (modifying its behavior) of the individual nodes in the intermediate inner or hidden layers so that the output matches the outputs of the training data. In other words, a neural network learns by being provided training data (learning examples) and eventually learns how to reach the correct output, even when it is presented with a new range or set of inputs. The series of mathematical operations, parameters, and/or weight factors learned during the training mode may be referred to herein as a "trained model." The trained model may then be applied to the new range or set of inputs in the prediction mode. A neural network may include, for example, without limitation, at least one of a Feedforward Neural Network (FNN), a Recurrent Neural Network (RNN), a Modular Neural Network (MNN), a Convolutional Neural Network (CNN), a fully Convolutional Neural Network (FCN), a Residual Neural Network (ResNet), an Ordinary Differential Equations Neural Networks (neural-ODE), a Deep Neural Network, or any other type of neural network.

Prediction of Visual Acuity Response

FIG. 1 is a block diagram of a prediction system 100 in accordance with various embodiments. Prediction system 100 is used to predict a visual acuity response (VAR) of one or more subjects in response to an AMD treatment. The AMD treatment may be, for example, but is not limited to, an anti-VEGF treatment such as ranibizumab, which may be administered via intravitreal injection or via another administration modality.

Prediction system 100 includes computing platform 102, data storage 104, and display system 106. Computing platform 102 may take various forms. In one or more embodiments, computing platform 102 includes a single computer (or computer system) or multiple computers in communication with each other. In other examples, computing platform 102 takes the form of a cloud computing platform. In some examples, computing platform 102 takes the form of a mobile computing platform (e.g., a smartphone, a tablet, a smartwatch, etc.).

Data storage 104 and display system 106 are each in communication with computing platform 102. In some examples, data storage 104, display system 106, or both may be considered part of or otherwise integrated with computing platform 102. Thus, in some examples, computing platform 102, data storage 104, and display system 106 may be separate components in communication with each other, but in other examples, some combination of these components may be integrated together.

Prediction system 100 includes data analyzer 108, which may be implemented using hardware, software, firmware, or a combination thereof. In one or more embodiments, data analyzer 108 is implemented in computing platform 102. Data analyzer 108 processes one or more inputs 110 using neural network system 112 to predict (or generate) a visual acuity response (VAR) output 114. VAR output 114 comprises a predicted change in the visual acuity of a subject undergoing treatment. In some embodiments, the one or more inputs 110 comprise a first input 110*a* and a second input 110*b*, as shown in FIG. 1. Such embodiments may be referred to herein as "multi-modal." In some embodiments, the one or more inputs 110 comprise a single input. Such embodiments may be referred to herein as "single mode."

Neural network system 112 may include any number of or combination of neural networks. In one or more embodiments, neural network system 112 takes the form of a convolutional neural network (CNN) system that includes one or more neural networks sub-systems. In some embodiments, at least one of these one or more neural network sub-systems may itself be a convolutional neural network. In other embodiments, at least one of these one or more neural network sub-systems may be a deep learning neural network (or deep neural network). In some embodiments, the neural network system 112 comprises a multi-modal neural network system described herein with respect to FIG. 3. In some embodiments, the neural network system 112 comprises a first single mode neural network system described herein with respect to FIG. 5. In some embodiments, the neural network system 112 comprises a second single mode neural network system described herein with respect to FIG. 7.

In a multi-modal approach, neural network system 112 may be trained via a single process in which the various portions of neural network system 112 are trained together (for instance, simultaneously). Thus, in the multi-modal approach, neural network system 112 does not require generating an output after a first training, integrating the output into neural network system 112, and then performing a second training. In the multi-modal approach, the entirety of neural network system 112 may be trained together (for instance, simultaneously), which may improve training efficiency and/or reduce the processing power needed for this training.

Multi-Modal Neural Networks

Figure 2:
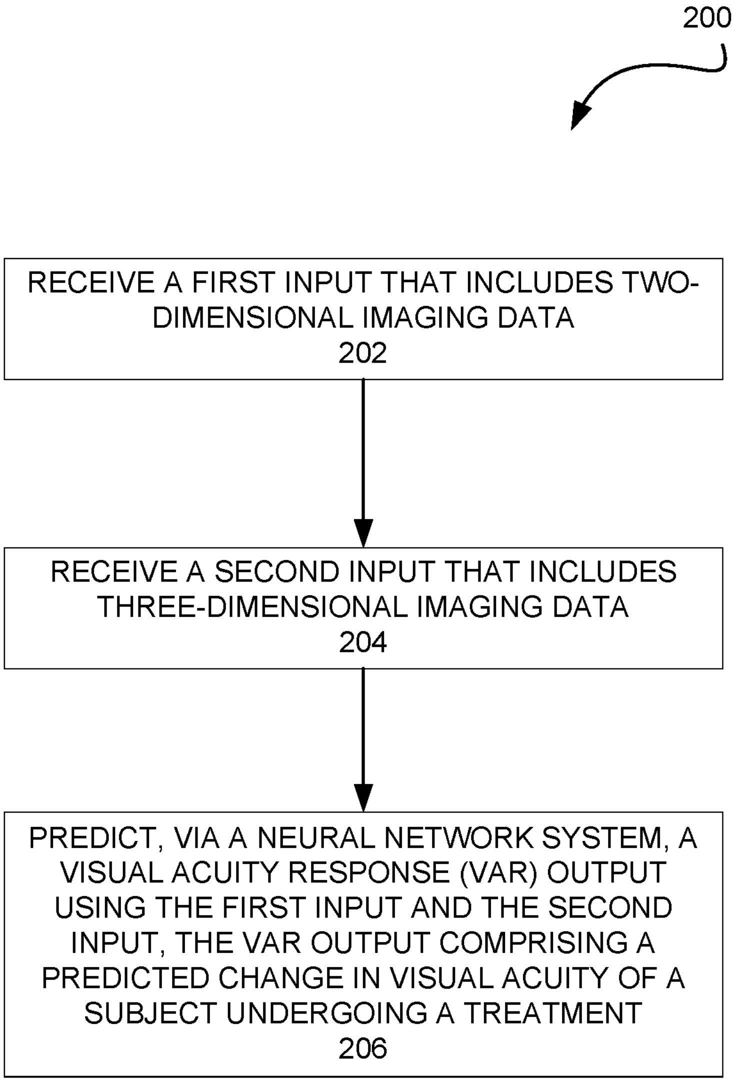
FIG. 2 is a flowchart of a multi-modal process for predicting visual acuity response, in accordance with various embodiments.

FIG. 2 is a flowchart of a multi-modal process 200 for predicting visual acuity response, in accordance with various embodiments. In one or more embodiments, process 200 is implemented using prediction system 100 described herein with respect to FIG. 1.

Step 202 includes receiving a first input that includes two-dimensional imaging data associated with a subject undergoing a treatment (such as an AMD treatment described herein). The two-dimensional imaging data may take the form of color fundus imaging data associated with the subject undergoing the treatment. For example, the color fundus imaging data may be color fundus images associated with the subject undergoing the treatment or data extracted from such color fundus images. The color fundus imaging data may be color fundus images of an eye of the subject undergoing the treatment or data extracted from such color fundus images.

Step 204 includes receiving a second input that includes three-dimensional imaging data associated with the subject undergoing the treatment into the neural network system. The three-dimensional imaging data may include OCT imaging data, may include data extracted from OCT images associated with the subject undergoing the treatment (e.g., OCT en-face images), may include tabular data extracted from such OCT images, or may include some other form of such OCT imaging data. The OCT imaging data may, for example, take the form of OCT images associated with the subject undergoing the treatment. The OCT imaging data may be OCT images of an eye of the subject undergoing the treatment or data extracted from such OCT images. In one or more embodiments, the second input includes other data associated with the subject undergoing the treatment such as, for example, but not limited to, visual acuity measurement data associated with the subject undergoing the treatment, demographic data associated with the subject undergoing the treatment, or both. The visual acuity measurement data may include one or more visual acuity measurements (such as a best corrected visual acuity (BCVA) measurement) associated with the subject undergoing the treatment. The demographic data may include, for example, age, gender, height, weight, or overall fitness level of the subject undergoing the treatment. In various embodiments, both the visual acuity measurement data and the demographic data are baseline data associated with the subject undergoing the treatment.

In one or more embodiments, the second input takes the form of tabular data that includes the BCVA measurement, the demographic data, and the three-dimensional imaging data (e.g., OCT thicknesses, OCT volumes, etc.). Because OCT images are large and complex, converting these OCT images into tabular form may help a neural network system to process the data contained in these images. In particular, by converting OCT imaging data into tabular form, the processing power and size of the portion of the neural network system that processes this tabular data may be reduced as compared to the processing of OCT images (e.g., OCT en-face images). These processing savings may allow the second input to be more easily integrated with the first input.

Step 206 includes predicting, via a neural network system, a visual acuity response (VAR) output using the first input and the second input, the VAR output comprising a predicted change in the visual acuity response of the subject undergoing the treatment. In some embodiments, the VAR output identifies the predicted change. In other embodiments, the VAR output corresponds to the predicted change in that the VAR output may be further processed to determine the predicted change. The predicted VAR output may correspond to a selected period of time after the initiation or administration of the AMD treatment. For example, the VAR output may enable prediction of a subject's visual acuity response at least about 3 months, 6 months, 9 months, 12 months, 18 months, or 24 months, or more after treatment has begun, at most about 24 months, 18 months, 12 months, 9 months, 6 months, 3 months, or less after treatment has begun, or a period of time after treatment has begun that is within a range defined by any two of the preceding values.

In one or more embodiments, predicting the VAR output includes generating, via the neural network system, a first output using the two-dimensional imaging data and generating, via the neural network system, a second output using the three-dimensional imaging data. In some embodiments, the VAR output is generated by fusion of the first output and the second output. That is, in some embodiments, the first output is generated using a first portion of the neural network system (such as the first neural network sub-system described herein with respect to FIG. 3) and the second output is generated using a second portion of the neural network system (such as the second neural network sub-system described herein with respect to FIG. 3). The first output and the second output may then be fused to form a fused input to a third portion of the neural network system (such as the third neural network sub-system described herein with respect to FIG. 3). The fused input may then be used by the third neural network sub-system to generate the VAR output that provides an indication with respect to the predicted change in the visual acuity of the subject.

In some embodiments, the first output comprises one or more features extracted from the two-dimensional imaging data. In some embodiments, the second output comprises one or more features extracted from the three-dimensional imaging data. The features extracted from the two-dimensional imaging data and the features extracted from the three-dimensional imaging data may then be fused together to form the fused input. The third portion of the neural network system can then generate the VAR output based on the fused input. In some embodiments, the features extracted from the two-dimensional imaging data and/or the features extracted from the three-dimensional imaging data are associated with regions containing abnormalities (such as lesions, abnormal bleeding, scar tissue, and/or tissue atrophy) on or in the eye of the subject, sizes of such regions, perimeters of such regions, areas of such regions, shape-descriptive features of such regions, distance of such regions to various features of the eye (such as a fovea, macula, retina, sclera, or choroid of the eye), contiguity of such regions, wedge-shaped subretinal hyporeflectivity, retinal pigment epithelium (RPE) attenuation and disruption, hyper-reflective foci, reticular pseudodrusen (RPD), multi-layer thickness reduction, photoreceptor atrophy, hypo-reflective cores in drusen, high central drusen volume, previous visual acuity, outer-retinal tubulation, choriocapillaris flow void, coloration of the two-dimensional imaging data and/or the three-dimensional imaging data or any region thereof, discoloration of the two-dimensional imaging data and/or the three-dimensional imaging data or any region thereof, or any combination of the preceding.

In some embodiments, the first and second outputs are fused to form an integrated multi-channel input that can undergo a subsequent feature extraction process by the third portion of the neural network system. Features extracted by the feature extraction process can then be used as a basis for generating the VAR output. The features extracted by the feature extraction process (and/or the fused input) can comprise or be associated with regions containing abnormalities (such as lesions, abnormal bleeding, scar tissue, and/or tissue atrophy) on or in the eye of the subject, sizes of such regions, perimeters of such regions, areas of such regions, shape-descriptive features of such regions, distance of such regions to various features of the eye (such as a fovea, macula, retina, sclera, or choroid of the eye), contiguity of such regions, wedge-shaped subretinal hyporeflectivity, retinal pigment epithelium (RPE) attenuation and disruption, hyper-reflective foci, reticular pseudodrusen (RPD), multi-layer thickness reduction, photoreceptor atrophy, hypo-reflective cores in drusen, high central drusen volume, previous visual acuity, outer-retinal tubulation, choriocapillaris flow void, coloration of the two-dimensional imaging data and/or the three-dimensional imaging data or any region thereof, discoloration of the two-dimensional imaging data and/or the three-dimensional imaging data or any region thereof, or any combination of the preceding.

In various embodiments, the VAR output is a value or score that identifies the predicted change in the visual acuity of the subject. For example, the VAR output may be a value or score that classifies the subject's visual acuity response with respect to the level of improvement predicted (e.g., letters of improvement) or decline (e.g., vision loss). As one specific example, the VAR output may be a predicted numeric change in BCVA that is later processed and identifies as belonging to one of a plurality of different classes of BCVA change, each class of BCVA change corresponding to a different range of letters of improvement. As another example, the VAR output may be the predicted class of change itself. In still other examples, the VAR output may be a predicted change in some other measure of visual acuity.

In other embodiments, the VAR output may be a value or representational output that requires one or more additional processing steps to arrive at the predicted change in visual acuity. For example, the VAR output may be a predicted, future BCVA of the subject at a period of time post-treatment (e.g., at least about 3 months, 6 months, 9 months, 12 months, 18 months, 24 months, or more post-treatment, at most about 24 months, 18 months, 12 months, 9 months, 6 months, 3 months, or less post-treatment, or a period of time post-treatment that is within a range defined by any two of the preceding values). The additional one or more processing steps may include computing the difference between the predicted, future BCVA and the baseline BCVA to determine the predicted change in visual acuity.

In some embodiments, the method further comprises, prior to receiving the first and second inputs, training the neural network system. In some embodiments, the neural network system is trained using two-dimensional data associated with a first plurality of subjects who have previously undergone the treatment and three-dimensional data associated with a second plurality of subjects who have previously undergone the treatment. The first and second pluralities may contain data associated with any number of subjects, such as at least about 1 thousand, 2 thousand, 3 thousand, 4 thousand, 5 thousand, 6 thousand, 7 thousand, 8 thousand, 9 thousand, 10 thousand, 20 thousand, 30 thousand, 40 thousand, 50 thousand, 60 thousand, 70 thousand, 80 thousand, 90 thousand, 100 thousand, 200 thousand, 300 thousand, 400 thousand, 500 thousand, 600 thousand, 700 thousand, 800 thousand, 900 thousand, 1 million, or more subjects, at most about 1 million, 900 thousand, 800 thousand, 700 thousand, 600 thousand, 500 thousand, 400 thousand, 300 thousand, 200 thousand, 100 thousand, 90 thousand, 80 thousand, 70 thousand, 60 thousand, 50 thousand, 40 thousand, 30 thousand, 20 thousand, 10 thousand, 9 thousand, 8 thousand, 7 thousand, 6 thousand, 5 thousand, 4 thousand, 3 thousand, 2 thousand, 1 thousand, or fewer subjects, or a number of subjects that is within a range defined by any two of the preceding values.

In some embodiments, the first and second pluralities are the same. That is, in some cases, the first and second pluralities comprise the exact same subjects. In some embodiments, the first and second pluralities are different. That is, in some cases, the first plurality comprises one or more subjects that are not featured in the second plurality, or vice versa. In some embodiments, the first and second pluralities are partially overlapping. That is, in some cases, one or more subjects are featured in both the first and second pluralities.

In some embodiments, training the neural network system further comprises using visual acuity measurements associated with the second plurality of subjects who have previously undergone the treatment, demographic data associated with the second plurality, or a combination thereof.

In some embodiments, the neural network system is trained using a focal loss, a cross-entropy loss, or a weighted cross-entropy loss.

Figure 3:
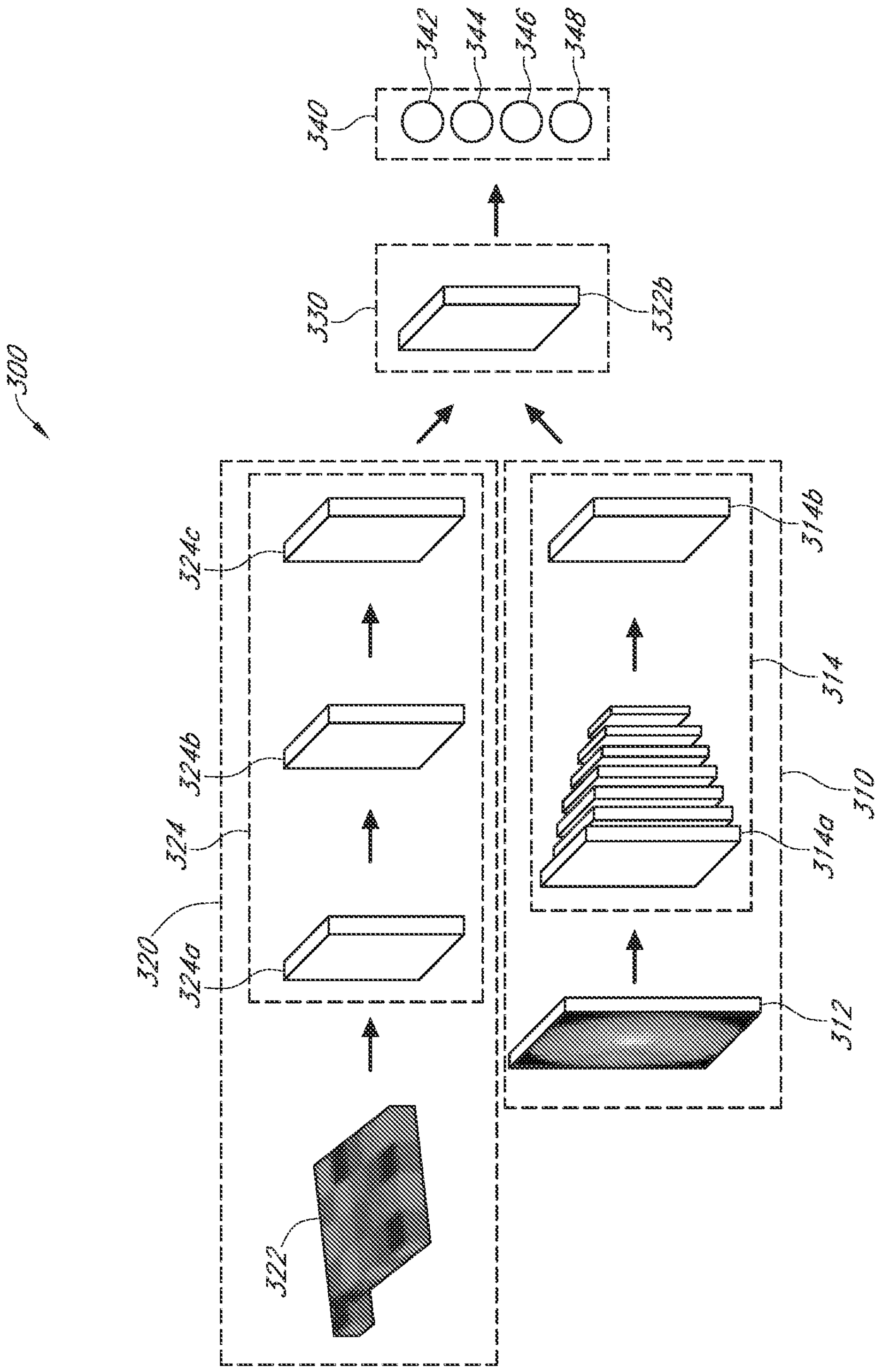
FIG. 3 is a block diagram of a multi-modal neural network system, in accordance with various embodiments.

FIG. 3 is a block diagram of a multi-modal neural network system 300. In some embodiments, the multi-modal neural network system is configured for use with the prediction system 100 described herein with respect to FIG. 1. In some embodiments, the multi-modal neural network system is configured to implement method 200 (or any of steps 202, 204, and 206) described herein with respect to FIG. 2.

In some embodiments, the multi-modal neural network system comprises a first neural network sub-system 310. In some embodiments, the first neural network sub-system comprises at least one first input layer 312 and at least one first dense inner layer 314. In some embodiments, the first input layer is configured to receive the first input described herein with respect to FIG. 2. In some embodiments, the at least one first dense inner layer is configured to apply a first trained model to the first input layer.

In the example shown, the at least one first dense inner layer comprises a trained image recognition model **314*a* and at least one output dense inner layer 314*b***. In some embodiments, the trained image recognition model is configured to apply an image recognition model to the first input layer. In some embodiments, the image recognition model comprises a pretrained image recognition model. In some embodiments, the pretrained image recognition model comprises a deep residual network, such as ResNet-34, ResNet-50, ResNet-101, or ResNet-152.

In some embodiments, the output dense inner layer receives output from the image recognition model and applies additional operations to the output from the image recognition model. In some embodiments, the additional operations are learned during training of the first trained model. In some embodiments, the image recognition model is not updated during training of the first trained model. In some embodiments, the output dense inner layer is configured to apply average pooling and/or softmax activation.

Although depicted as comprising a single output dense inner layer in FIG. 3, the at least one output dense inner layer may comprise any number of dense inner layers. In some embodiments, the at least one output dense inner layer comprises at least about 1, 2, 3, 4, 5, 6, 7, 8, 9, 10, 20, 30, 40, 50, 60, 70, 80, 90, 100, or more dense inner layers, at most about 100, 90, 80, 70, 60, 50, 40, 30, 20, 10, 9, 8, 7, 6, 5, 4, 3, 2, or 1 dense inner layers, or a number of dense inner layers that is within a range defined by any two of the preceding values. Each of the output dense inner layers may be configured to apply average pooling, rectified linear (ReLu) activation, and/or softmax activation.

In some embodiments, the multi-modal neural network system comprises a second neural network sub-system 320. In some embodiments, the second neural network sub-system comprises at least one second input layer 322 and at least one second dense inner layer 324. In some embodiments, the second input layer is configured to receive the second input described herein with respect to FIG. 2. In some embodiments, the at least one second dense inner layer is configured to apply a second trained model to the second input layer.

In the example shown, the at least one second dense inner layer comprises three dense inner layers 324*a*, 324*b*, and 324*c*. In some embodiments, dense inner layer 324*a* is configured to apply a first set of operations to the second input layer. In some embodiments, dense inner layer 324*b* is configured to apply a second set of operations to dense inner layer 324*a*. In some embodiments, dense inner layer 324*c* is configured to apply a third set of operations to dense inner layer 324*b*. In some embodiments, the first, second, and third sets of operations are learned during training of the second trained model. In some embodiments, dense inner layers 324*a* and 324*b* are configured to apply ReLu activation and dense inner layer 324*c* is configured to apply softmax activation.

Although depicted as comprising three second dense inner layers in FIG. 3, the at least one second dense inner layer may comprise any number of dense inner layers. In some embodiments, the at least one second dense inner layer comprises at least about 1, 2, 3, 4, 5, 6, 7, 8, 9, 10, 20, 30, 40, 50, 60, 70, 80, 90, 100, or more dense inner layers, at most about 100, 90, 80, 70, 60, 50, 40, 30, 20, 10, 9, 8, 7, 6, 5, 4, 3, 2, or 1 dense inner layers, or a number of dense inner layers that is within a range defined by any two of the preceding values. Each of the second dense inner layers may be configured to apply average pooling, rectified linear (ReLu) activation, and/or softmax activation.

In some embodiments, the multi-modal neural network system comprises a third neural network sub-system 330. In some embodiments, the third neural network sub-system comprises at least one third dense inner layer 332. In some embodiments, the third at least one third dense inner layer is configured to receive a first output from the at least first dense inner layer associated with the first neural network sub-system and to receive a second output from the at least second dense inner layer associated with the second neural network sub-system.

In the example shown, the at least one third dense inner layer comprises a single layer. In some embodiments, the single layer is configured to apply a set of operations to the first and second outputs. In some embodiments, the set of operations is learned during training of the third trained model. In some embodiments, the third dense inner layer is configured to apply softmax activation.

Although depicted as comprising a single third dense inner layer in FIG. 3, the at least one third dense inner layer may comprise any number of dense inner layers. In some embodiments, the at least one third dense inner layer comprises at least about 1, 2, 3, 4, 5, 6, 7, 8, 9, 10, 20, 30, 40, 50, 60, 70, 80, 90, 100, or more dense inner layers, at most about 100, 90, 80, 70, 60, 50, 40, 30, 20, 10, 9, 8, 7, 6, 5, 4, 3, 2, or 1 dense inner layers, or a number of dense inner layers that is within a range defined by any two of the preceding values. Each of the third dense inner layers may be configured to apply average pooling, rectified linear (ReLu) activation, and/or softmax activation.

In some embodiments, the neural network system is configured to output classification data 340. In some embodiments, the classification data comprises a first likelihood 342 that the subject undergoing the treatment is likely to achieve a score of less than 5 letters, a second likelihood 344 that the subject undergoing the treatment is likely to achieve a score of 5-9 letters, a third likelihood 346 that the subject undergoing the treatment is likely to achieve a score of 10-14 letters, and/or a fourth likelihood 348 that the subject undergoing the treatment is likely to achieve a score of more than 15 letters on a visual acuity measurement a period of time after the treatment. In some embodiments, the output classification data are arranged as an output layer of the neural network system.

Although depicted as comprising 4 classes in FIG. 3, the classification data may comprise any number of classes. For example, the classification data may comprise at least about 2, 3, 4, 5, 6, 7, 8, 9, 10, 11, 12, 13, 14, 15, 16, 17, 18, 19, 20, or more classes, at most about 20, 19, 18, 17, 16, 15, 14, 13, 12, 11, 10, 9, 8, 7, 6, 5, 4, 3, or 2 classes, or a number of classes that is within a range defined by any two of the preceding values. For instance, the classification data may comprise first and second likelihoods that the subject undergoing the treatment is likely to achieve a score of less than 10 letters and a score of more than 11 letters, respectively. As a further example, the classification data may comprise first, second, third, fourth, fifth, sixth, seventh, eighth, ninth, tenth, and eleventh likelihoods that the subject undergoing the treatment is likely to achieve a score of less than 2 letters, a score of 2-3 letters, a score of 4-5 letters, a score of 6-7 letters, a score of 8-9 letters, a score of 10-11 letters, a score of 12-13 letters, a score of 14-15 letters, a score of 16-17 letters, a score of 18-19 letters, and a score of more than 20 letters, respectively. A person having skill in the art will recognize that many variations are possible.

In some embodiments, the first, second, and third trained models are trained together. In some embodiments, the first, second, and third trained models are trained simultaneously. For instance, in some embodiments, training data in the form of two-dimensional imaging data associated with the first plurality of subjects who have previously undergone the treatment is provided to the first neural network sub-system while training data in the form of three-dimensional imaging data associated with the first plurality of subjects who have previously undergone the treatment is simultaneously provided to the second neural network sub-system. The first, second, and third models associated with the first, second, and third neural network sub-systems, respectively, are then trained simultaneously. In this manner, the multi-modal neural network system may be trained end-to-end without requiring distinct, standalone, or sequential training of its components.

In some embodiments, the neural network system is configured to apply an exemplary attention gate mechanism.

Single Mode Neural Network Using Two-Dimensional Data

Figure 4:
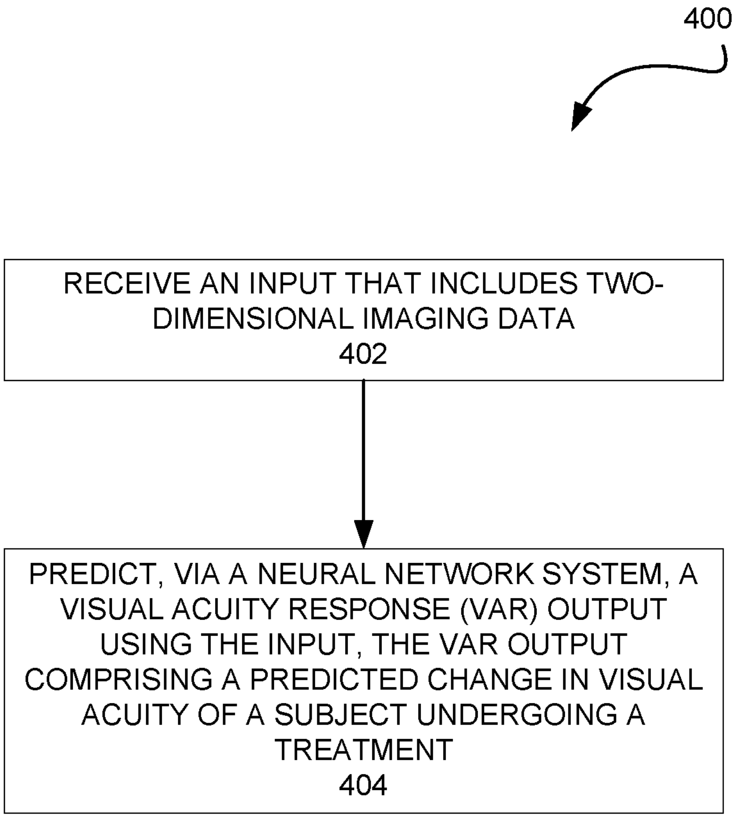
FIG. 4 is a flowchart of a first single mode process for predicting visual acuity response, in accordance with various embodiments.

FIG. 4 is a flowchart of a first single mode process 400 for predicting visual acuity response, in accordance with various embodiments. In one or more embodiments, process 400 is implemented using prediction system 100 described herein with respect to FIG. 1.

Step 402 includes receiving an input that includes two-dimensional imaging data associated with a subject undergoing a treatment (such as an AMD treatment described herein). The two-dimensional imaging data may take the form of any two-dimensional imaging data described herein (such as any two-dimensional imaging data described herein with respect to FIG. 1, 2, or 3).

Step 404 includes predicting, via a neural network system, a visual acuity response (VAR) output using the input, the VAR output comprising a predicted change in the visual acuity response of the subject undergoing the treatment. In some embodiments, the VAR output comprises any VAR output described herein (such as any VAR output described herein with respect to FIG. 1, 2, or 3).

In some embodiments, the method further comprises, prior to receiving the first and second inputs, training the neural network system. In some embodiments, the neural network system is trained using two-dimensional data associated with a plurality of subjects who have previously undergone the treatment. The plurality may contain data associated with any number of subjects, such as at least about 1 thousand, 2 thousand, 3 thousand, 4 thousand, 5 thousand, 6 thousand, 7 thousand, 8 thousand, 9 thousand, 10 thousand, 20 thousand, 30 thousand, 40 thousand, 50 thousand, 60 thousand, 70 thousand, 80 thousand, 90 thousand, 100 thousand, 200 thousand, 300 thousand, 400 thousand, 500 thousand, 600 thousand, 700 thousand, 800 thousand, 900 thousand, 1 million, or more subjects, at most about 1 million, 900 thousand, 800 thousand, 700 thousand, 600 thousand, 500 thousand, 400 thousand, 300 thousand, 200 thousand, 100 thousand, 90 thousand, 80 thousand, 70 thousand, 60 thousand, 50 thousand, 40 thousand, 30 thousand, 20 thousand, 10 thousand, 9 thousand, 8 thousand, 7 thousand, 6 thousand, 5 thousand, 4 thousand, 3 thousand, 2 thousand, 1 thousand, or fewer subjects, or a number of subjects that is within a range defined by any two of the preceding values.

Figure 5:
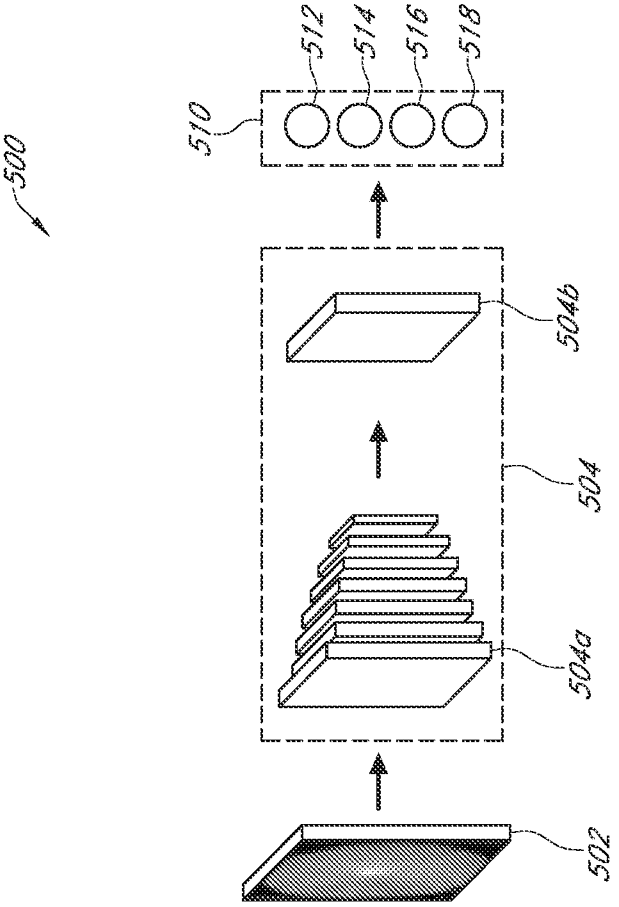
FIG. 5 is a block diagram of a first single mode neural network system, in accordance with various embodiments.

FIG. 5 is a block diagram of a first single mode neural network system 500. In some embodiments, the first single mode neural network system is configured for use with the prediction system 100 described herein with respect to FIG. 1. In some embodiments, the first single mode neural network system is configured to implement method 400 (or any of steps 402 and 404) described herein with respect to FIG. 4.

In some embodiments, the first single mode neural network system comprises at least one input layer 502 and at least one dense inner layer 504. In some embodiments, the input layer is configured to receive the input described herein with respect to FIG. 4. In some embodiments, the at least one dense inner layer is configured to apply a trained model to the input layer.

In the example shown, the at least one dense inner layer comprises a trained image recognition model 504*a* and at least one output dense inner layer 504*b*. In some embodiments, the trained image recognition model is configured to apply an image recognition model to the input layer. In some embodiments, the image recognition model comprises any image recognition model described herein (such as any image recognition model described herein with respect to FIG. 3).

In some embodiments, the output dense inner layer receives output from the image recognition model and applies additional operations to the output from the image recognition model. In some embodiments, the additional operations are learned during training of the trained model. In some embodiments, the image recognition model is not updated during training of the trained model. In some embodiments, the output dense inner layer is configured to apply average pooling and/or softmax activation.

Although depicted as comprising a single output dense inner layer in FIG. 5, the at least one output dense inner layer may comprise any number of dense inner layers. In some embodiments, the at least one output dense inner layer comprises at least about 1, 2, 3, 4, 5, 6, 7, 8, 9, 10, 20, 30, 40, 50, 60, 70, 80, 90, 100, or more dense inner layers, at most about 100, 90, 80, 70, 60, 50, 40, 30, 20, 10, 9, 8, 7, 6, 5, 4, 3, 2, or 1 dense inner layers, or a number of dense inner layers that is within a range defined by any two of the preceding values. Each of the output dense inner layers may be configured to apply average pooling, rectified linear (ReLu) activation, and/or softmax activation.

In some embodiments, the neural network system is configured to output classification data 510. In some embodiments, the classification data comprises a first likelihood 512 that the subject undergoing the treatment is likely to achieve a score of less than 5 letters, a second likelihood 514 that the subject undergoing the treatment is likely to achieve a score of 5-9 letters, a third likelihood 516 that the subject undergoing the treatment is likely to achieve a score of 10-14 letters, and/or a fourth likelihood 518 that the subject undergoing the treatment is likely to achieve a score of more than 15 letters on a visual acuity measurement a period of time after the treatment. In some embodiments, the output classification data are arranged as an output layer of the neural network system.

Although depicted as comprising 4 classes in FIG. 5, the classification data may comprise any number of classes, as described herein (for example, as described herein with respect to FIG. 3).

In some embodiments, the neural network system is configured to apply an exemplary attention gate mechanism.

Single Mode Neural Network Using Three-Dimensional Data

Figure 6:
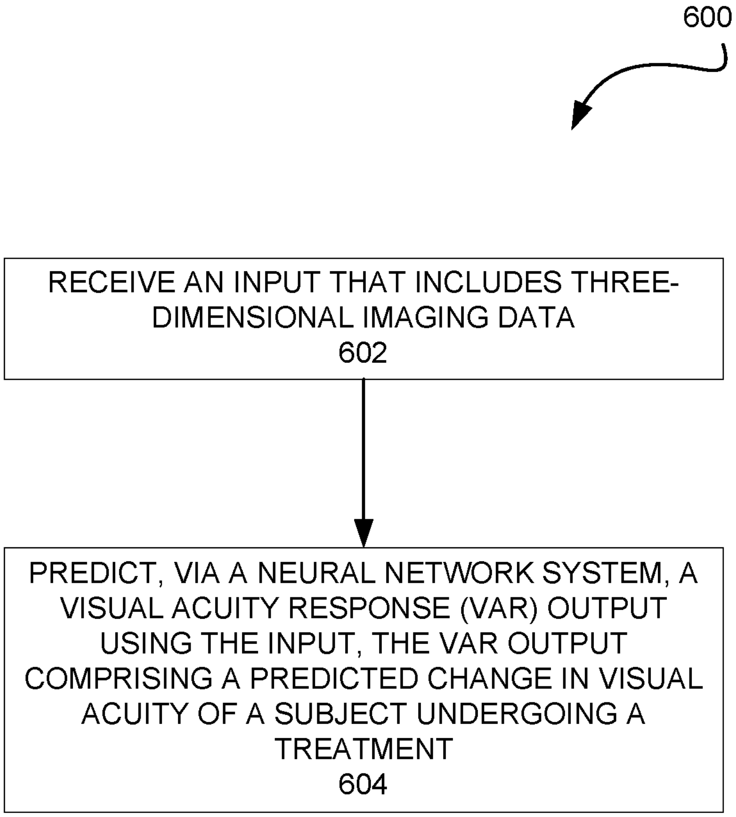
FIG. 6 is a flowchart of a second single mode process for predicting visual acuity response, in accordance with various embodiments.

FIG. 6 is a flowchart of a second single mode process 600 for predicting visual acuity response, in accordance with various embodiments. In one or more embodiments, process 600 is implemented using prediction system 100 described herein with respect to FIG. 1.

Step 602 includes receiving an input that includes three-dimensional imaging data associated with the subject undergoing the treatment into the neural network system. The three-dimensional imaging data may comprise any three-dimensional imaging data described herein (such as any three-dimensional imaging data described herein with respect to FIG. 1, 2, or 3).

Step 604 includes predicting, via a neural network system, a visual acuity response (VAR) output using the input, the VAR output comprising a predicted change in the visual acuity response of the subject undergoing the treatment. In some embodiments, the VAR output comprises any VAR output described herein (such as any VAR output described herein with respect to FIG. 1, 2, or 3).

In some embodiments, the method further comprises, prior to receiving the first and second inputs, training the neural network system. In some embodiments, the neural network system is trained using three-dimensional data associated with a plurality of subjects who have previously undergone the treatment. The plurality may contain data associated with any number of subjects, such as at least about 1 thousand, 2 thousand, 3 thousand, 4 thousand, 5 thousand, 6 thousand, 7 thousand, 8 thousand, 9 thousand, 10 thousand, 20 thousand, 30 thousand, 40 thousand, 50 thousand, 60 thousand, 70 thousand, 80 thousand, 90 thousand, 100 thousand, 200 thousand, 300 thousand, 400 thousand, 500 thousand, 600 thousand, 700 thousand, 800 thousand, 900 thousand, 1 million, or more subjects, at most about 1 million, 900 thousand, 800 thousand, 700 thousand, 600 thousand, 500 thousand, 400 thousand, 300 thousand, 200 thousand, 100 thousand, 90 thousand, 80 thousand, 70 thousand, 60 thousand, 50 thousand, 40 thousand, 30 thousand, 20 thousand, 10 thousand, 9 thousand, 8 thousand, 7 thousand, 6 thousand, 5 thousand, 4 thousand, 3 thousand, 2 thousand, 1 thousand, or fewer subjects, or a number of subjects that is within a range defined by any two of the preceding values.

Figure 7:
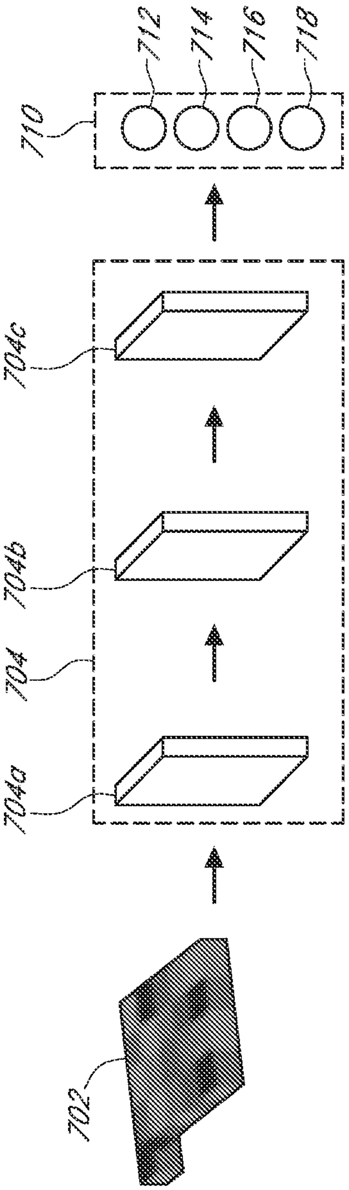
FIG. 7 is a block diagram of a second single mode neural network system, in accordance with various embodiments.

FIG. 7 is a block diagram of a second single mode neural network system 700. In some embodiments, the second single mode neural network system is configured for use with the prediction system 100 described herein with respect to FIG. 1. In some embodiments, the second single mode neural network system is configured to implement method 600 (or any of steps 602 and 604) described herein with respect to FIG. 6.

In some embodiments, the second single model neural network system comprises at least one input layer 702 and at least one dense inner layer 704. In some embodiments, the input layer is configured to receive the input described herein with respect to FIG. 6. In some embodiments, the at least one dense inner layer is configured to apply a trained model to the input layer.

In the example shown, the at least one dense inner layer comprises three dense inner layers 704*a*, 704*b*, and 704*c*. In some embodiments, dense inner layer 704*a* is configured to apply a first set of operations to the input layer. In some embodiments, dense inner layer 704*b* is configured to apply a second set of operations to dense inner layer 704*a*. In some embodiments, dense inner layer 704*c* is configured to apply a third set of operations to dense inner layer 704*b*. In some embodiments, the first, second, and third sets of operations are learned during training of the trained model. In some embodiments, dense inner layers 704*a* and 704*b* are configured to apply ReLu activation and dense inner layer 704*c* is configured to apply softmax activation.

Although depicted as comprising three dense inner layers in FIG. 7, the at least one dense inner layer may comprise any number of dense inner layers. In some embodiments, the at least one dense inner layer comprises at least about 1, 2, 3, 4, 5, 6, 7, 8, 9, 10, 20, 30, 40, 50, 60, 70, 80, 90, 100, or more dense inner layers, at most about 100, 90, 80, 70, 60, 50, 40, 30, 20, 10, 9, 8, 7, 6, 5, 4, 3, 2, or 1 dense inner layers, or a number of dense inner layers that is within a range defined by any two of the preceding values. Each of the dense inner layers may be configured to apply average pooling, rectified linear (ReLu) activation, and/or softmax activation.

In some embodiments, the neural network system is configured to output classification data 710. In some embodiments, the classification data comprises a first likelihood 712 that the subject undergoing the treatment is likely to achieve a score of less than 5 letters, a second likelihood 714 that the subject undergoing the treatment is likely to achieve a score of 5-9 letters, a third likelihood 716 that the subject undergoing the treatment is likely to achieve a score of 10-14 letters, and/or a fourth likelihood 718 that the subject undergoing the treatment is likely to achieve a score of more than 15 letters on a visual acuity measurement a period of time after the treatment. In some embodiments, the output classification data are arranged as an output layer of the neural network system.

Although depicted as comprising 4 classes in FIG. 7, the classification data may comprise any number of classes, as described herein (for example, as described herein with respect to FIG. 3).

In some embodiments, the neural network system is configured to apply an exemplary attention gate mechanism.

In some embodiments, the systems and methods described herein are used to provide treatment recommendations. For instance, in some embodiments, the neural network systems are configured to generate a treatment output based on the VAR output. In some embodiments, the treatment output indicates a predicted change in visual acuity of a subject in response to the treatment. In some embodiments, a treatment recommendation is provided to a medical provided based on the treatment output. In some embodiments, the treatment recommendation prompts the medical provider to administer the treatment to the subject in response to the treatment output being an improvement in the visual acuity of the subject. In some embodiments, the step of administering the treatment comprises intravitreal administration of the treatment or a derivative thereof at a therapeutic dosage. In some embodiments, the treatment is ranibizumab and the therapeutic dosage is 0.3 milligrams (mg) or 0.5 mg

EXAMPLES

Example 1: Prediction of Visual Acuity Response in the CATT Study

Deep learning (DL) were developed models to predict visual acuity response (VAR) to ranibizumab (RBZ) by using baseline (BL) characteristics and color fundus images (CFIs) of patients with neovascular age-related macular degeneration. VAR was formulated as a classification problem with 4 classes (class 1=<5 letters, class 2=5-9 letters, class 3=10-14 letters, and class 4=≥15 letters). Each class was assigned based on best-corrected visual acuity (BCVA) change from BL to Month 12. To solve the classification problem, 3 DL models were designed that processed data from different modalities (the two-dimensional and three-dimensional imaging modalities described herein). Two different single mode models (as described herein with respect to FIGS. 4 and 5, and FIGS. 6 and 7, respectively) were trained to process BL characteristics including BCVA, age, and CFI or optical coherence tomography (OCT) imaging biomarkers. The third model fused the 2 sub-networks to produce the final classification, as described herein with respect to FIGS. 2 and 3. Example attention mechanisms were exploited to enhance relevant parts of input data and to improve performance of the models. Data were divided into training, validation, and testing sets in a 3:1:1 ratio. Table 1 shows the loss type, number of epochs, and optimizer employed during training of each model.

TABLE 1

Loss type, number of epochs, and optimizer employed for each model

| | Training Details | | |
|---|---|---|---|
| | Loss Type | Number of Epochs | Optimizer (lr) |
| OCT model | Weighted cross-entropy | 100 | SGD (0.01) |
| CFI model | Focal loss | 100 | Adam (0.01) |
| Multi-modal model | Focal loss | 100 | Adam (0.001) |

The study was a retrospective analysis of BL data from 284 patients receiving RBZ monthly treatment in the randomized Comparison of Age Related Macular Degeneration Treatment Trials (CATT) study (NCT00593450). The CATT study aimed to assess the relative efficacy and safety of RBZ and bevacizumab with monthly and as-needed regimens. The distribution across the 4 classes was imbalanced, with 64, 43, 52, and 125 patients in classes 1, 2, 3, and 4, respectively. The performance was assessed based on validation (N=56) and test (N=57) data subsets using accuracy and area under the receiver operating characteristic (AUROC) curve. Additionally, macro F1 (mF1) scores, per-class F1-scores, and area under the precision-recall (AUCPR) curve were calculated to provide a more informative assessment of model performance.

Table 2 shows a variety of performance measures for the 3 models. Performance measures varied considerably among the 3 models (e.g., mF1 scores of the test dataset were 0.332, 0.236, and 0.354 for OCT, CFI, and multi-modal models, respectively). Additionally, individual per-class results showed large variation, reflecting the presence of a strong class imbalance in the data.

TABLE 2

Model performance measures on validation and test data

| | Validation dataset | | | Test dataset | | |
|---|---|---|---|---|---|---|
| | OCT model | CFI model | Multi-modal model | OCT model | CFI model | Multi-modal model |
| mF1 score | 0.444 | 0.295 | 0.416 | 0.332 | 0.236 | 0.354 |
| AUCPR | 0.386 | 0.299 | 0.381 | 0.405 | 0.31 | 0.451 |
| Accuracy | 0.471 | 0.354 | 0.45 | 0.471 | 0.317 | 0.484 |
| AUROC | 0.669 | 0.578 | 0.665 | 0.702 | 0.577 | 0.659 |
| Class 1: F1 score | 0.271 | 0.305 | 0.317 | 0.267 | 0.362 | 0.338 |
| Class 2: F1 score | 0.355 | 0.044 | 0.455 | 0.293 | 0.091 | 0.48 |
| Class 3: F1 score | 0.533 | 0.396 | 0.323 | 0.133 | 0.024 | 0.0 |
| Class 4: F1 score | 0.615 | 0.433 | 0.569 | 0.634 | 0.469 | 0.599 |

Table 3 shows the performance of the 3 models on a test data subset comprising a study group subjected to monthly RBZ injections. Results are presented for models with and without application of the exemplary attention mechanism. Table 4 shows the performance of the 3 models on a test data subset comprising all study arms without application of the exemplary attention mechanism.

TABLE 3

Evaluation results on RBZ monthly injections study group with and without (in parentheses) application of an exemplary attention mechanism

| | OCT model | CFI model | Multi-modal model |
|---|---|---|---|
| mF1 score | 0.39 (0.33) | 0.24 (0.24) | 0.4 (0.35) |
| AUCPR | 0.42 (0.41) | 0.3 (0.31) | 0.37 (0.45) |
| Accuracy | 0.47 (0.47) | 0.33 (0.32) | 0.43 (0.48) |
| AUROC | 0.69 (0.7) | 0.56 (0.57) | 0.66 (0.66) |
| Class 1: F1 score | 0.29 (0.27) | 0.26 (0.36) | 0.33 (0.34) |
| Class 2: F1 score | 0.46 (0.29) | 0.03 (0.09) | 0.42 (0.48) |
| Class 3: F1 score | 0.22 (0.13) | 0.17 (0.02) | 0.29 (0.0) |
| Class 4: F1 score | 0.61 (0.63) | 0.5 (0.47) | 0.54 (0.6) |

TABLE 4

Evaluation results on all study arms without application of an exemplary attention mechanism

| | OCT model | CFI model | Multi-modal model |
|---|---|---|---|
| mF1 score | 0.31 | 0.29 | 0.35 |
| AUCPR | 0.38 | 0.34 | 0.4 |
| Accuracy | 0.45 | 0.37 | 0.4 |
| AUROC | 0.66 | 0.6 | 0.64 |
| Class 1: F1 score | 0.13 | 0.32 | 0.21 |
| Class 2: F1 score | 0.26 | 0.2 | 0.28 |
| Class 3: F1 score | 0.24 | 0.12 | 0.34 |
| Class 4: F1 score | 0.63 | 0.52 | 0.56 |

As shown in Tables 1-4, the multi-modal model outperformed the CFI and, to a lesser extent, the OCT models in many performance measures. However, for certain performance measures, the CFI or OCT models provided the best performance. Thus, all three models presented herein may be useful, depending on the particular problem of interest.

Computer Implemented System

Figure 8:
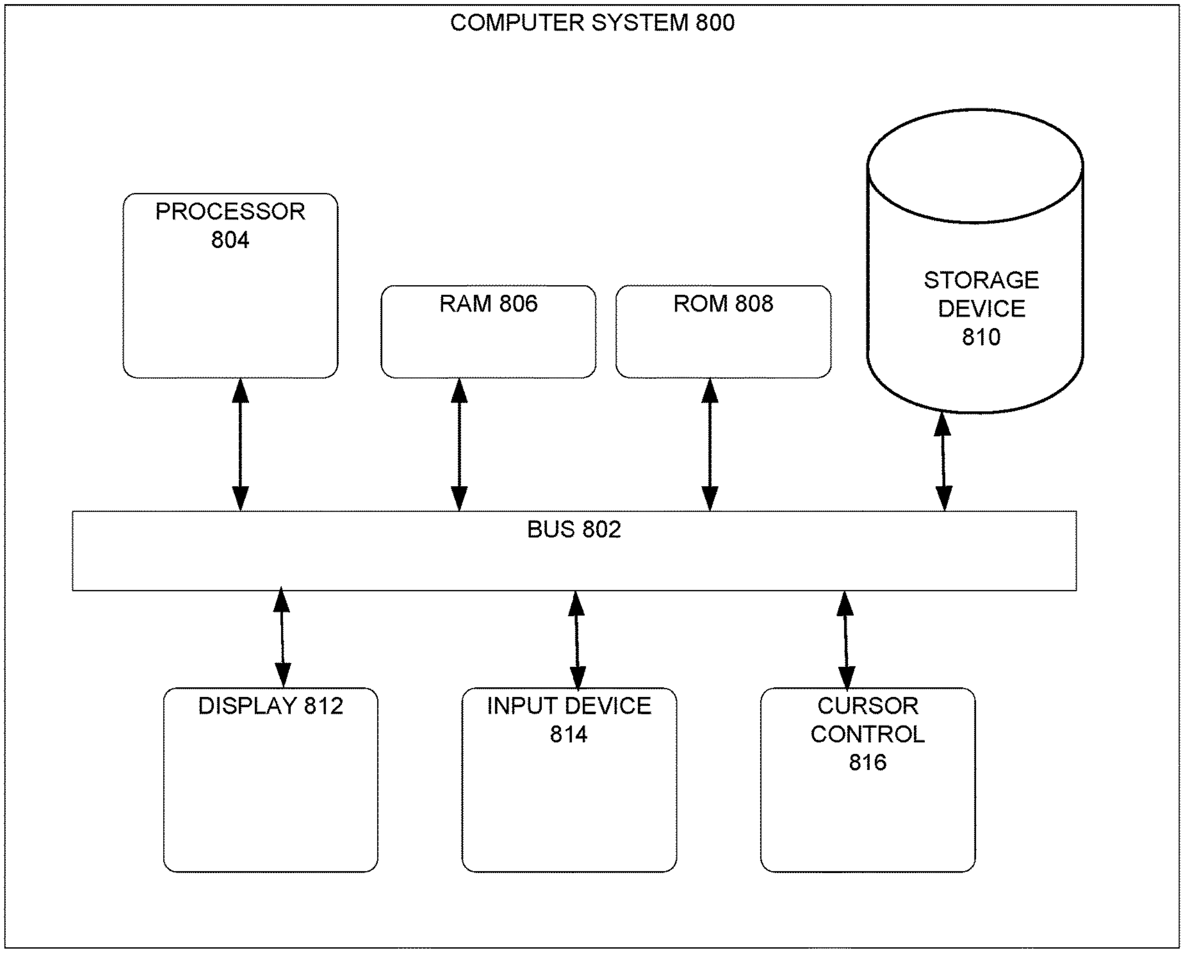
FIG. 8 is a block diagram of a computer system in accordance with various embodiments.

FIG. 8 is a block diagram of a computer system in accordance with various embodiments. Computer system 800 may be an example of one implementation for computing platform 102 described above in FIG. 1. In one or more examples, computer system 800 can include a bus 802 or other communication mechanism for communicating information, and a processor 804 coupled with bus 802 for processing information. In various embodiments, computer system 800 can also include a memory, which can be a random-access memory (RAM) 806 or other dynamic storage device, coupled to bus 802 for determining instructions to be executed by processor 804. Memory also can be used for storing temporary variables or other intermediate information during execution of instructions to be executed by processor 804. In various embodiments, computer system 800 can further include a read only memory (ROM) 808 or other static storage device coupled to bus 802 for storing static information and instructions for processor 804. A storage device 810, such as a magnetic disk or optical disk, can be provided and coupled to bus 802 for storing information and instructions.

In various embodiments, computer system 800 can be coupled via bus 802 to a display 812, such as a cathode ray tube (CRT) or liquid crystal display (LCD), for displaying information to a computer user. An input device 814, including alphanumeric and other keys, can be coupled to bus 802 for communicating information and command selections to processor 804. Another type of user input device is a cursor control 816, such as a mouse, a joystick, a trackball, a gesture input device, a gaze-based input device, or cursor direction keys for communicating direction information and command selections to processor 804 and for controlling cursor movement on display 812. This input device 814 typically has two degrees of freedom in two axes, a first axis (e.g., x) and a second axis (e.g., y), that allows the device to specify positions in a plane. However, it should be understood that input devices 814 allowing for three-dimensional (e.g., x, y and z) cursor movement are also contemplated herein.

Consistent with certain implementations of the present teachings, results can be provided by computer system 800 in response to processor 804 executing one or more sequences of one or more instructions contained in RAM 806 or in response to special-purpose processing units executing one or more sequences of one or more instructions contained in the dedicated RAM of these special-purpose processing units. Such instructions can be read into RAM 806 from another computer-readable medium or computer-readable storage medium, such as storage device 810. Execution of the sequences of instructions contained in RAM 806 can cause processor 804 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, storage device, data storage device, etc.) or "computer-readable storage medium" as used herein refers to any media that participates in providing instructions to processor 804 for execution. Such a medium can take many forms, including but not limited to, non-volatile media, volatile media, and transmission media. Examples of non-volatile media can include, but are not limited to, optical, solid state, magnetic disks, such as storage device 810. Examples of volatile media can include, but are not limited to, dynamic memory, such as RAM 806. Examples of transmission media can include, but are not limited to, coaxial cables, copper wire, and fiber optics, including the wires that comprise bus 802.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 804 of computer system 800 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, optical communications connections, etc.

It should be appreciated that the methodologies described herein, flow charts, diagrams, and accompanying disclosure can be implemented using computer system 800 as a standalone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, graphical processing units (GPUs), tensor processing units (TPUs), artificial intelligence (AI) accelerator ASICs, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 800, whereby processor 804 would execute the analyses and determinations provided by these engines, subject to instructions provided by any one of, or a combination of, the memory components RAM 806, ROM, 808, or storage device 810 and user input provided via input device 814.

CONCLUSION

While the present teachings are described in conjunction with various embodiments, it is not intended that the present teachings be limited to such embodiments. On the contrary, the present teachings encompass various alternatives, modifications, and equivalents, as will be appreciated by those of skill in the art.

For example, the flowcharts and block diagrams described above illustrate the architecture, functionality, and/or operation of possible implementations of various method and system embodiments. Each block in the flowcharts or block diagrams may represent a module, a segment, a function, a portion of an operation or step, or a combination thereof. In some alternative implementations of an embodiment, the function or functions noted in the blocks may occur out of the order noted in the figures. For example, in some cases, two blocks shown in succession may be executed substantially concurrently or integrated in some manner. In other cases, the blocks may be performed in the reverse order. Further, in some cases, one or more blocks may be added to replace or supplement one or more other blocks in a flowchart or block diagram.

Thus, in describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

RECITATION OF EMBODIMENTS

Embodiment. 1. A method for predicting a visual acuity response, the method comprising:

receiving a first input that includes two-dimensional imaging data associated with a subject undergoing a treatment;

receiving a second input that includes three-dimensional imaging data associated with the subject undergoing the treatment; and predicting, via a neural network system, a visual acuity response (VAR) output using the first input and the second input, the VAR output comprising a predicted change in visual acuity of the subject undergoing the treatment in response to the treatment.

Embodiment 2. The method of Embodiment 1, wherein the three-dimensional imaging data comprises optical coherence tomography (OCT) imaging data associated with the subject undergoing the treatment and wherein the two-dimensional imaging data comprises color fundus imaging data associated with the subject undergoing the treatment.

Embodiment 3. The method of Embodiment 1 or 2, wherein the second input further includes a visual acuity measurement associated with the subject undergoing the treatment and demographic data associated with the subject undergoing the treatment.

Embodiment 4. The method of any one of Embodiments 1-3, wherein the predicting, via the neural network system, the VAR output comprises:

generating a first output using the two-dimensional imaging data associated with the subject undergoing the treatment;

generating a second output using the three-dimensional imaging data associated with the subject undergoing the treatment; and generating the VAR output via fusion of the first output and the second output.

Embodiment 5. The method of any one of Embodiments 1-4, wherein the neural network system comprises:

a first neural network sub-system comprising at least one first input layer and at least one first dense inner layer, the at least one first input layer configured to receive the first input, the at least one first dense inner layer configured to apply a first trained model to the first input layer;

a second neural network sub-system comprising at least one second input layer and at least one second dense inner layer, the at least one second input layer configured to receive the first input, the at least one second dense inner layer configured to apply a second trained model to the second input layer; and a third neural network sub-system comprising at least one third dense inner layer configured to receive a first output from the at least first dense inner layer and a second output from the at least second dense layer and to apply a third trained model to the first and second outputs to thereby predict the VAR output.

Embodiment 6. The method of Embodiment 5, wherein the at least one first dense inner layer comprises a trained image recognition model and an output dense inner layer and wherein the at least one second dense inner layer comprises a plurality of second dense inner layers.

Embodiment 7. The method of any one of Embodiments 1-6, further comprising, prior to the receiving the first input and to receiving the second input, training the neural network system using two-dimensional imaging data associated with a first plurality of subjects who have previously undergone the treatment and three-dimensional imaging data associated with a second plurality of subjects who have previously undergone the treatment.

Embodiment 8. The method of Embodiment 7, wherein the training the neural network system further comprises using visual acuity measurements associated with the second plurality of subjects who have previously undergone the treatment, demographic data associated with the second plurality of subjects who have previously undergone the treatment, or a combination thereof.

Embodiment 9. A system for predicting visual acuity response, the system comprising:

a non-transitory memory; and one or more processors coupled to the non-transitory memory and configured to read instructions from the non-transitory memory to cause the system to perform operations comprising:

receiving a first input that includes two-dimensional imaging data associated with a subject undergoing a treatment;

receiving a second input that includes three-dimensional imaging data associated with the subject undergoing the treatment; and predicting, via a neural network system, a visual acuity response (VAR) output using the first input and the second input, the VAR output comprising a predicted change in visual acuity of the subject undergoing the treatment in response to the treatment.

Embodiment 10. The system of Embodiment 9, wherein the three-dimensional imaging data comprises optical coherence tomography (OCT) imaging data associated with the subject undergoing the treatment and wherein the two-dimensional imaging data comprises color fundus imaging data associated with the subject undergoing the treatment.

Embodiment 11. The system of Embodiment 9 or 10, wherein the second input further includes a visual acuity measurement associated with the subject undergoing the treatment and demographic data associated with the subject undergoing the treatment.

Embodiment 12. The system of any one of Embodiments 9-11, wherein the predicting, via the neural network system, the VAR output comprises:

generating a first output using the two-dimensional imaging data associated with the subject undergoing the treatment;

generating a second output using the three-dimensional imaging data associated with the subject undergoing the treatment; and generating the VAR output via fusion of the first output and the second output.

Embodiment 13. The system of any one of Embodiments 9-12, wherein the neural network system comprises:

a first neural network sub-system comprising at least one first input layer and at least one first dense inner layer, the at least one first input layer configured to receive the first input, the at least one first dense inner layer configured to apply a first trained model to the first input layer;

a second neural network sub-system comprising at least one second input layer and at least one second dense inner layer, the at least one second input layer configured to receive the first input, the at least one second dense inner layer configured to apply a second trained model to the second input layer; and a third neural network sub-system comprising at least one third dense inner layer configured to receive a first output from the at least first dense inner layer and a second output from the at least second dense layer and to apply a third trained model to the first and second outputs to thereby predict the VAR output.

Embodiment 14. The system of Embodiment 13, wherein the at least one first dense inner layer comprises a trained image recognition model and an output dense inner layer and wherein the at least one second dense inner layer comprises a plurality of second dense inner layers.

Embodiment 15. The system of any one of Embodiments 9-14, wherein the operations further comprise, prior to the receiving the first input and to receiving the second input, training the neural network system using two-dimensional imaging data associated with a first plurality of subjects who have previously undergone the treatment and three-dimensional imaging data associated with a second plurality of subjects who have previously undergone the treatment.

Embodiment 16. The system of Embodiment 15, wherein the training the neural network system further comprises using visual acuity measurements associated with the second plurality of subjects who have previously undergone the treatment, demographic data associated with the second plurality of subjects who have previously undergone the treatment, or a combination thereof.

Embodiment 17. A non-transitory, machine-readable medium having stored thereon machine-readable instructions executable to cause a system to perform operations comprising:

receiving a first input that includes two-dimensional imaging data associated with a subject undergoing a treatment;

receiving a second input that includes three-dimensional imaging data associated with the subject undergoing the treatment; and predicting, via a neural network system, a visual acuity response (VAR) output using the first input and the second input, the VAR output comprising a predicted change in visual acuity of the subject undergoing the treatment in response to the treatment.

Embodiment 18. The non-transitory, machine-readable medium of Embodiment 17, wherein the three-dimensional imaging data comprises optical coherence tomography (OCT) imaging data associated with the subject undergoing the treatment and wherein the two-dimensional imaging data comprises color fundus imaging data associated with the subject undergoing the treatment.

Embodiment 19. The non-transitory, machine-readable medium of Embodiment 17 or 18, wherein the second input further includes a visual acuity measurement associated with the subject undergoing the treatment and demographic data associated with the subject undergoing the treatment.

Embodiment 20. The non-transitory, machine-readable medium of any one of Embodiments 17-19, wherein the predicting, via the neural network system, the VAR output comprises:

generating a first output using the two-dimensional imaging data associated with the subject undergoing the treatment;

generating a second output using the three-dimensional imaging data associated with the subject undergoing the treatment; and generating the VAR output via fusion of the first output and the second output.

Embodiment 21. The non-transitory, machine-readable medium of any one of Embodiments 17-20, wherein the neural network system comprises:

a first neural network sub-system comprising at least one first input layer and at least one first dense inner layer, the at least one first input layer configured to receive the first input, the at least one first dense inner layer configured to apply a first trained model to the first input layer;

a second neural network sub-system comprising at least one second input layer and at least one second dense inner layer, the at least one second input layer configured to receive the first input, the at least one second dense inner layer configured to apply a second trained model to the second input layer; and a third neural network sub-system comprising at least one third dense inner layer configured to receive a first output from the at least first dense inner layer and a second output from the at least second dense layer and to apply a third trained model to the first and second outputs to thereby predict the VAR output.

Embodiment 22. The non-transitory, machine-readable medium of Embodiment 21, wherein the at least one first dense inner layer comprises a trained image recognition model and an output dense inner layer and wherein the at least one second dense inner layer comprises a plurality of second dense inner layers.

Embodiment 23. The non-transitory, machine-readable medium of any one of Embodiments 17-22, wherein the operations further comprise, prior to the receiving the first input and to receiving the second input, training the neural network system using two-dimensional imaging data associated with a first plurality of subjects who have previously undergone the treatment and three-dimensional imaging data associated with a second plurality of subjects who have previously undergone the treatment.

Embodiment 24. The non-transitory, machine-readable medium of Embodiment 23, wherein the training the neural network system further comprises using visual acuity measurements associated with the second plurality of subjects who have previously undergone the treatment, demographic data associated with the second plurality of subjects who have previously undergone the treatment, or a combination thereof.

Embodiment 25. A method for predicting a visual acuity response, the method comprising:

receiving an input that includes two-dimensional imaging data associated with a subject undergoing a treatment; and predicting, via a neural network system, a visual acuity response (VAR) output using the input, the VAR output comprising a predicted change in visual acuity of the subject undergoing the treatment in response to the treatment.

Embodiment 26. The method of Embodiment 25, wherein the two-dimensional imaging data comprises color fundus imaging data associated with the subject undergoing the treatment.

Embodiment 27. The method of Embodiment 25 or 26, wherein the neural network system comprises:

at least one input layer configured to receive the input; and at least one dense inner layer configured to apply a trained model to the input layer, to thereby predict the VAR output.

Embodiment 28. The method of Embodiment 27, wherein the at least one dense inner layer comprises a trained image recognition model and an output dense inner layer.

Embodiment 29. The method of any one of Embodiments 25-28, further comprising, prior to the receiving the input, training the neural network system using two-dimensional imaging data associated with a plurality of subjects who have previously undergone the treatment.

Embodiment 30. A system for predicting visual acuity response, the system comprising:

a non-transitory memory; and one or more processors coupled to the non-transitory memory and configured to read instructions from the non-transitory memory to cause the system to perform operations comprising:

receiving an input that includes two-dimensional imaging data associated with a subject undergoing a treatment; and predicting, via a neural network system, a visual acuity response (VAR) output using the input, the VAR output comprising a predicted change in visual acuity of the subject undergoing the treatment in response to the treatment.

Embodiment 31. The system of Embodiment 30, wherein the two-dimensional imaging data comprises color fundus imaging data associated with the subject undergoing the treatment.

Embodiment 32. The system of Embodiment 30 or 31, wherein the neural network system comprises:

at least one input layer configured to receive the input; and at least one dense inner layer configured to apply a trained model to the input layer, to thereby predict the VAR output.

Embodiment 33. The system of Embodiment 32, wherein the at least one dense inner layer comprises a trained image recognition model and an output dense inner layer.

Embodiment 34. The system of any one of Embodiments 30-33, wherein the operations further comprise, prior to the receiving the input, training the neural network system using two-dimensional imaging data associated with a plurality of subjects who have previously undergone the treatment.

Embodiment 35. The system of Embodiment 34, wherein the training the neural network system further comprises using visual acuity measurements associated with the second plurality of subjects who have previously undergone the treatment, demographic data associated with the second plurality of subjects who have previously undergone the treatment, or a combination thereof.

Embodiment 36. A non-transitory, machine-readable medium having stored thereon machine-readable instructions executable to cause a system to perform operations comprising:

receiving an input that includes two-dimensional imaging data associated with a subject undergoing a treatment; and predicting, via a neural network system, a visual acuity response (VAR) output using the input, the VAR output comprising a predicted change in visual acuity of the subject undergoing the treatment in response to the treatment.

Embodiment 37. The non-transitory, machine-readable medium of Embodiment 36, wherein the two-dimensional imaging data comprises color fundus imaging data associated with the subject undergoing the treatment.

Embodiment 38. The non-transitory, machine-readable medium of Embodiment 36 or 37, wherein the neural network system comprises:

at least one input layer configured to receive the input; and at least one dense inner layer configured to apply a trained model to the input layer, to thereby predict the VAR output.

Embodiment 39. The non-transitory, machine-readable medium of Embodiment 38, wherein the at least one dense inner layer comprises a trained image recognition model and an output dense inner layer.

Embodiment 40. The non-transitory, machine-readable medium of any one of Embodiments 36-39, wherein the operations further comprise, prior to the receiving the input, training the neural network system using two-dimensional imaging data associated with a plurality of subjects who have previously undergone the treatment.

Embodiment 41. A method for predicting a visual acuity response, the method comprising:

receiving an input that includes three-dimensional imaging data associated with a subject undergoing a treatment; and predicting, via a neural network system, a visual acuity response (VAR) output using the input, the VAR output comprising a predicted change in visual acuity of the subject undergoing the treatment in response to the treatment.

Embodiment 42. The method of Embodiment 41, wherein the three-dimensional imaging data comprises optical coherence tomography (OCT) imaging data associated with the subject undergoing the treatment.

Embodiment 43. The method of Embodiment 41 or 42, wherein the input further includes a visual acuity measurement associated with the subject undergoing the treatment and demographic data associated with the subject undergoing the treatment.

Embodiment 44. The method of any one of Embodiments 41-3, wherein the neural network system comprises:

at least one input layer configured to receive the input; and at least one dense inner layer configured to apply a trained model to the input layer, to thereby predict the VAR output.

Embodiment 45. The method of Embodiment 44, wherein the at least one dense inner layer comprises a plurality of dense inner layers.

Embodiment 46. The method of any one of Embodiments 41-45, further comprising, prior to the receiving the input, training the neural network system using three-dimensional imaging data associated with a plurality of subjects who have previously undergone the treatment.

Embodiment 47. The method of Embodiment 46, wherein the training the neural network system further comprises using visual acuity measurements associated with the plurality of subjects who have previously undergone the treatment, demographic data associated with the plurality of subjects who have previously undergone the treatment, or a combination thereof.

Embodiment 48. A system for predicting visual acuity response, the system comprising:

a non-transitory memory; and one or more processors coupled to the non-transitory memory and configured to read instructions from the non-transitory memory to cause the system to perform operations comprising:

receiving an input that includes three-dimensional imaging data associated with a subject undergoing a treatment; and predicting, via a neural network system, a visual acuity response (VAR) output using the input, the VAR output comprising a predicted change in visual acuity of the subject undergoing the treatment in response to the treatment.

Embodiment 49. The system of Embodiment 48, wherein the three-dimensional imaging data comprises optical coherence tomography (OCT) imaging data associated with the subject undergoing the treatment.

Embodiment 50. The system of Embodiment 48 or 49, wherein the input further includes a visual acuity measurement associated with the subject undergoing the treatment and demographic data associated with the subject undergoing the treatment.

Embodiment 51. The system of any one of Embodiments 48-50, wherein the neural network system comprises:

at least one input layer configured to receive the input; and at least one dense inner layer configured to apply a trained model to the input layer, to thereby predict the VAR output.

Embodiment 52. The system of Embodiment 51, wherein the at least one dense inner layer comprises a plurality of dense inner layers.

Embodiment 53. The system of any one of Embodiments 48-52, wherein the operations further comprise, prior to the receiving the input, training the neural network system using three-dimensional imaging data associated with a plurality of subjects who have previously undergone the treatment.

Embodiment 54. The system of Embodiment 53, wherein the training the neural network system further comprises using visual acuity measurements associated with the plurality of subjects who have previously undergone the treatment, demographic data associated with the plurality of subjects who have previously undergone the treatment, or a combination thereof.

Embodiment 55. A non-transitory, machine-readable medium having stored thereon machine-readable instructions executable to cause a system to perform operations comprising:

receiving an input that includes three-dimensional imaging data associated with a subject undergoing a treatment; and predicting, via a neural network system, a visual acuity response (VAR) output using the input, the VAR output comprising a predicted change in visual acuity of the subject undergoing the treatment in response to the treatment.

Embodiment 56. The non-transitory, machine-readable medium of Embodiment 55, wherein the three-dimensional imaging data comprises optical coherence tomography (OCT) imaging data associated with the subject undergoing the treatment.

Embodiment 57. The non-transitory, machine-readable medium of Embodiment 55 or 56, wherein the input further includes a visual acuity measurement associated with the subject undergoing the treatment and demographic data associated with the subject undergoing the treatment.

Embodiment 58. The non-transitory, machine-readable medium of any one of Embodiments 55-57, wherein the neural network system comprises:

at least one input layer configured to receive the input; and at least one dense inner layer configured to apply a trained model to the input layer, to thereby predict the VAR output.

Embodiment 59. The non-transitory, machine-readable medium of Embodiment 58, wherein the at least one dense inner layer comprises a plurality of dense inner layers.

Embodiment 60. The non-transitory, machine-readable medium of any one of Embodiments 55-59, wherein the operations further comprise, prior to the receiving the input, training the neural network system using three-dimensional imaging data associated with a plurality of subjects who have previously undergone the treatment.

Embodiment 61. The non-transitory, machine-readable medium of Embodiment 60, wherein the training the neural network system further comprises using visual acuity measurements associated with the plurality of subjects who have previously undergone the treatment, demographic data associated with the plurality of subjects who have previously undergone the treatment, or a combination thereof.

Embodiment 62. A method for treating a subject diagnosed with a nAMD condition, comprising:

receiving a first input that includes two-dimensional imaging data associated with a subject;

receiving a second input that includes three-dimensional imaging data associated with the subject;

generating, via a trained neural network system, a treatment output using the first input and the second input, the treatment output indicating a predicted change in visual acuity of the subject in response to the treatment;

based on the treatment output, providing a treatment recommendation to a medical provider, the treatment recommendation prompting the medical provider to:

administer the treatment to the subject in response to the treatment output being an improvement in the visual acuity of the subject, the step of administering the treatment comprising intravitreal administration of the treatment or a derivative thereof at a therapeutic dosage, wherein the treatment is ranibizumab and the therapeutic dosage is 0.3 milligrams (mg) or 0.5 mg.

The invention claimed is:

1. A method for predicting a visual acuity response, the method comprising:

receiving a first input that includes two-dimensional imaging data associated with a subject undergoing a treatment;

receiving a second input that includes three-dimensional imaging data associated with the subject undergoing the treatment; and predicting, via a neural network system, a visual acuity response (VAR) output using the first input and the second input, the VAR output comprising a predicted change in visual acuity of the subject undergoing the treatment, wherein the neural network system comprises:

a first neural network sub-system comprising at least one first input layer and at least one first dense inner layer, the at least one first input layer configured to receive the first input, the at least one first dense inner layer configured to apply a first trained model to the first input layer;

a second neural network sub-system comprising at least one second input layer and at least one second dense inner layer, the at least one second input layer configured to receive the second input, the at least one second dense inner layer configured to apply a second trained model to the second input layer; and a third neural network sub-system comprising at least one third dense inner layer configured to receive a first output from the at least first dense inner layer and a second output from the at least second dense layer and to apply a third trained model to the first and second outputs to thereby predict the VAR output.

2. The method of claim 1, wherein the three-dimensional imaging data comprises optical coherence tomography (OCT) imaging data associated with the subject undergoing the treatment and wherein the two-dimensional imaging data comprises color fundus imaging data associated with the subject undergoing the treatment.

3. The method of claim 1, wherein the second input further includes a visual acuity measurement associated with the subject undergoing the treatment and demographic data associated with the subject undergoing the treatment.

4. The method of claim 1, wherein the predicting, via the neural network system, the VAR output comprises:

generating the first output using the two-dimensional imaging data associated with the subject undergoing the treatment and the first neural network sub-system;

generating the second output using the three-dimensional imaging data associated with the subject undergoing the treatment and the second neural network sub-system; and generating the VAR output via fusion of the first output and the second output.

5. The method of claim 1, wherein the at least one first dense inner layer comprises a trained image recognition model and an output dense inner layer, or wherein the at least one second dense inner layer comprises a plurality of second dense inner layers.

6. The method of claim 1, further comprising, training the neural network system using two-dimensional imaging data associated with a first plurality of subjects who have previously undergone the treatment and using three-dimensional imaging data associated with a second plurality of subjects who have previously undergone the treatment.

7. The method of claim 1, wherein the VAR output comprises a predicted numeric change in best corrected visual acuity ("BCVA") or one of a plurality of different classes of BCVA change.

8. The method of claim 1, further comprising converting the three-dimensional imaging data associated with the subject undergoing the treatment into tabular form to generate the second input.

9. A system for predicting visual acuity response, the system comprising:

a non-transitory memory; and one or more processors coupled to the non-transitory memory and configured to read instructions from the non-transitory memory to cause the system to perform operations comprising:

receiving a first input that includes two-dimensional imaging data associated with a subject undergoing a treatment;

receiving a second input that includes three-dimensional imaging data associated with the subject undergoing the treatment; and predicting, via a neural network system, a visual acuity response (VAR) output using the first input and the second input, the VAR output comprising a predicted change in visual acuity of the subject undergoing the treatment, wherein the neural network system comprises:

a first neural network sub-system comprising at least one first input layer and at least one first dense inner layer, the at least one first input layer configured to receive the first input, the at least one first dense inner layer configured to apply a first trained model to the first input layer;

a second neural network sub-system comprising at least one second input layer and at least one second dense inner layer, the at least one second input layer configured to receive the second input, the at least one second dense inner layer configured to apply a second trained model to the second input layer; and a third neural network sub-system comprising at least one third dense inner layer configured to receive a first output from the at least first dense inner layer and a second output from the at least second dense layer and to apply a third trained model to the first and second outputs to thereby predict the VAR output.

10. The system of claim 9, wherein the three-dimensional imaging data comprises optical coherence tomography (OCT) imaging data associated with the subject undergoing the treatment and wherein the two-dimensional imaging data comprises color fundus imaging data associated with the subject undergoing the treatment.

11. The system of claim 9, wherein the second input further includes a visual acuity measurement associated with the subject undergoing the treatment and demographic data associated with the subject undergoing the treatment.

12. The system of claim 9, wherein the predicting, via the neural network system, the VAR output comprises:

generating the first output using the two-dimensional imaging data associated with the subject undergoing the treatment and the first neural network sub-system;

generating the second output using the three-dimensional imaging data associated with the subject undergoing the treatment and the second neural network sub-system; and generating the VAR output via fusion of the first output and the second output.

13. The system of claim 8, wherein the at least one first dense inner layer comprises a trained image recognition model and an output dense inner layer or wherein the at least one second dense inner layer comprises a plurality of second dense inner layers.

14. The system of claim 8, wherein the operations further comprise training the neural network system using two-dimensional imaging data associated with a first plurality of subjects who have previously undergone the treatment and using three-dimensional imaging data associated with a second plurality of subjects who have previously undergone the treatment.

15. The system of claim 9, wherein the operations further comprise: converting the three-dimensional imaging data associated with the subject undergoing the treatment into tabular form to generate the second input.

16. A non-transitory, machine-readable medium having stored thereon machine-readable instructions executable to cause a system to perform operations comprising:

receiving a first input that includes two-dimensional imaging data associated with a subject undergoing a treatment;

receiving a second input that includes three-dimensional imaging data associated with the subject undergoing the treatment; and predicting, via a neural network system, a visual acuity response (VAR) output using the first input and the second input, the VAR output comprising a predicted change in visual acuity of the subject undergoing the treatment, wherein the neural network system comprises:

a first neural network sub-system comprising at least one first input layer and at least one first dense inner layer, the at least one first input layer configured to receive the first input, the at least one first dense inner layer configured to apply a first trained model to the first input layer;

a second neural network sub-system comprising at least one second input layer and at least one second dense inner layer, the at least one second input layer configured to receive the second input, the at least one second dense inner layer configured to apply a second trained model to the second input layer; and a third neural network sub-system comprising at least one third dense inner layer configured to receive a first output from the at least first dense inner layer and a second output from the at least second dense layer and to apply a third trained model to the first and second outputs to thereby predict the VAR output.

17. The non-transitory, machine-readable medium of claim 16, wherein the three-dimensional imaging data comprises optical coherence tomography (OCT) imaging data associated with the subject undergoing the treatment and wherein the two-dimensional imaging data comprises color fundus imaging data associated with the subject undergoing the treatment.

18. The non-transitory, machine-readable medium of claim 16, wherein the second input further includes a visual acuity measurement associated with the subject undergoing the treatment and demographic data associated with the subject undergoing the treatment.

19. The non-transitory, machine-readable medium of claim 16, wherein the predicting, via the neural network system, the VAR output comprises:

generating the first output using the two-dimensional imaging data associated with the subject undergoing the treatment and the first neural network sub-system;

generating the second output using the three-dimensional imaging data associated with the subject undergoing the treatment and the second neural network sub-system; and generating the VAR output via fusion of the first output and the second output.

20. The non-transitory, machine-readable medium of claim 16, wherein the at least one first dense inner layer comprises a trained image recognition model and an output dense inner layer or wherein the at least one second dense inner layer comprises a plurality of second dense inner layers.

21. The non-transitory, machine-readable medium of claim 16, wherein the operations further comprise:

converting the three-dimensional imaging data associated with the subject undergoing the treatment into tabular form to generate the second input.

* * * * *